United States Patent [19]

Bennett, deceased et al.

[11] Patent Number: Plant 7,189

[45] Date of Patent: Mar. 13, 1990

[54] MINIATURE ROSE PLANT NAMED 'RUTHIE'

[76] Inventors: Cecilia L. D. Bennett, deceased, late of Chula Vista, Calif.; by Susan M. O'Brien, executrix, 489 Minot Ave., Chula Vista, Calif. 92010

[21] Appl. No.: 293,175

[22] Filed: Jan. 3, 1989

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant, named 'Ruthie', which is characterized by its blooms of near White to near Naples Yellow with a soft blush of near Poppy Red to near Carmine on the outer margins. The blooms are usually borne one to a stem with hybrid tea form but on occasion may be produced in sprays of 3 to 5 or more. The bush is vigorous, well-branched and produces moderate to heavy quantity of very fragrant blooms.

1 Drawing Sheet

The present invention relates to a new and distinct variety of a hardy, dwarf, bush plant of the miniature class; the variety being primarily characterized as white.

The variety is further characterized by:

Long stemmed blooms of hybrid tea-type form, borne usually one to a stem but on occasion in sprays of 3 to 5 or more. The blooms are held very erect and well above the foliage.

It has a heavy damask fragrance.

The plant ranges in height from 24 to 36 inches (60 to 90 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The seed parent was Sonia (U.S. Plant Pat. No. 3,095), and the pollen parent was Little Melody (miniature rose plant, pink blend; Leslie Strawn; introduced by Tiny Petals Nursery, 1979). It differs from its seed parent in the following ways. It is a miniature rose of near white with a pink blush, and Sonia is a floribunda of pink blend with no white present on the blooms. It differs from its pollen parent in the following ways. It produces a very tall, vigorous bush and blooms of near white with a pink blush; and Little Melody is a small, compact bush plant with blooms of pale pink with a pale yellow base.

BRIEF DESCRIPTION OF THE DRAWING

The single color photographic view shows, in plan view, three flowers of the claimed plant 'Ruthie' in various stages of maturity from early bud stage to nearly full blown stage.

BOTANICAL DESCRIPTION

The descrptive matter which follows pertains to roses grown in the months of March through November 1988. The plants were grown outdoors in Chula Vista, Calif., and are believed to be accurate standards for this cultivar in similar conditions of soil and climate elsewhere.

Referring now specifically to the new and distinct variety of miniature rose plant named 'Ruthie', the following is a detailed description thereof in outline; all major color plate identifications being by reference to the British Colour Council Horticultural Colour Chart, except where common terms of color definition are employed.

Type: Hardy, dwarf, bushy, greenhouse or outdoor, exhibition or garden decorative potted plant.

Class: Miniature.

Variety name: Ruthie.

Flowers Borne: Usually one to a stem, but occasionally in sprays of 3 to 5 or more on erect stems with foliage well below the blooms.

Quantity of bloom: Moderate to heavy both outdoors or greenhouse grown.

Bud:

- Peduncle.—Average length (40 to 60 mm); average diameter and sturdy; ranging from near Scheeles Green (860/3 to 860/1 page 175) to near Spinach Green (0960/2 to 0960/1 page 0960) with occasional tinting of bronze.
- *Hairs.*—Extremely small and reddish; located over the surface of the peduncle but none on the calyx tube.
- *Calyx.*—Color range same as the peduncle.
- *Opening.*—Opens well in all weather.

Bloom: *Size when fully open.*—Large for a miniature variety (50 to 70 mm).

- *Petalage.*—Double—25 to 30 petals, arranged regularly, plus 5 to 10 petaloids.
- *Form.*—Urn-shaped to ovoid as the bloom progresses. The petals remain somewhat cupped with the apex and/or margins reflexed outward, becoming at maturity more loosely cupped.

Petals: Fairly thick with good substance; both the upper and under surfaces of all petals have a matte finish.

- *Shape.*—Outer petals are of a broad obovate form with a slight peak at the apex. The intermediate petals are very much like the outer petals only narrower. The inner petals are a broad lanceolate form; and the petaloids are also lanceolate with some occasional irregularities.

Color: Newly opened flowers from plants grown outdoors (March through November of 1988), Chula Vista, Calif.

*All petals.*—Upper and under surfaces — Ranging from near Naples Yellow (403/3 to 403/1 page 121) with a blush on the outer margins of each petal of near Poppy Red (16/3 to 16/2 page 16) when the bloom is first open to near White with a blush of near Carmine (21/3 to 21/2 page 21) on the margins of each petal when the bloom is open more than one day. (*Note: The blush of near Poppy Red to near Carmine only occurs on blooms exposed to the sun. During overcast weather or when a bloom is opened indoors, little or no blush is present on the margins of the petals.).

*General color effect.*—Newly opened flowers — Pale cream-yellow with a slight blush of pink on the outer margin of petals. One day open — Fading to near white with a deeper pink blush on the margins. Three days open — White bloom with deep pink margins on all petals exposed to the sun. (*Note: No blush of pink will be present on blooms opened indoors or with little sunlight).

*Flower longevity.*—(March through November 1988) Plant in pot 3 to 5 days from bud with sepals reflexed to fully opened bloom. Holding at fully open with colors as described above for 3 to 5 days or longer. Cut bloom at livingroom temperature 5 to 7 days or longer.

Reproductive organs:

*Stamens.*—A generous amount arranged uniformly around the pistil.

*Filaments.*—Varying in length with shorter filaments more proximal to the pistil; golden yellow in color with anthers also of golden yellow.

*Pollen.*—Abundant.

*Pistil.*—Short, spreading and abundant; pale yellow in color.

*Ovaries.*—All encased in calyx.

*Hips.*—Some.

*Seeds.*—3 to 5 or more in each hip.

*Sepals.*—Permanent; spear-shaped; open as the bloom opens.

Foliage:

*Leaves.*—Five to seven leaflets on the average; medium size for a miniature rose plant.

*Leaflets.*—Broad ovate-shaped.

*Margins.*—Very serrated with tinting of bronze, especially noticeable on the newer foliage.

*Color.*—Color range same as the peduncle. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few is any hairs but does contain 2 to 5 small thorns.

*Stipules.*—Varying in length from small to medium; average width; tapering auricles angled outward at about 45 degrees.

Growth:

*Habit.*—Dwarf, bushy; tall height for a miniature rose plant.

*Growth.*—Vigorous and well-branched.

*Canes.*—Medium diameter; sturdy; very erect.

*Main stems.*—Color range same as the peduncle.

*Thorns.*—Averaging 10 to 15 per 10 cm on the main stems and fewer than 5 per 10 cm on the branches. Pale yellow in color; small to average in size; hooked slightly downward.

*Branches.*—Color range same as the peduncle.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named, 'Ruthie' of hardy, dwarf, vigorous growth, well-branched and attractive in appearance, substantially as illustrated and described, characterized by its hybrid tea-form blooms, ranging from near Naples Yellow to White with a blush of near Poppy Red to near Carmine, with flowers borne usually one to a stem but occasionally in sprays of 3 to 5 or more.

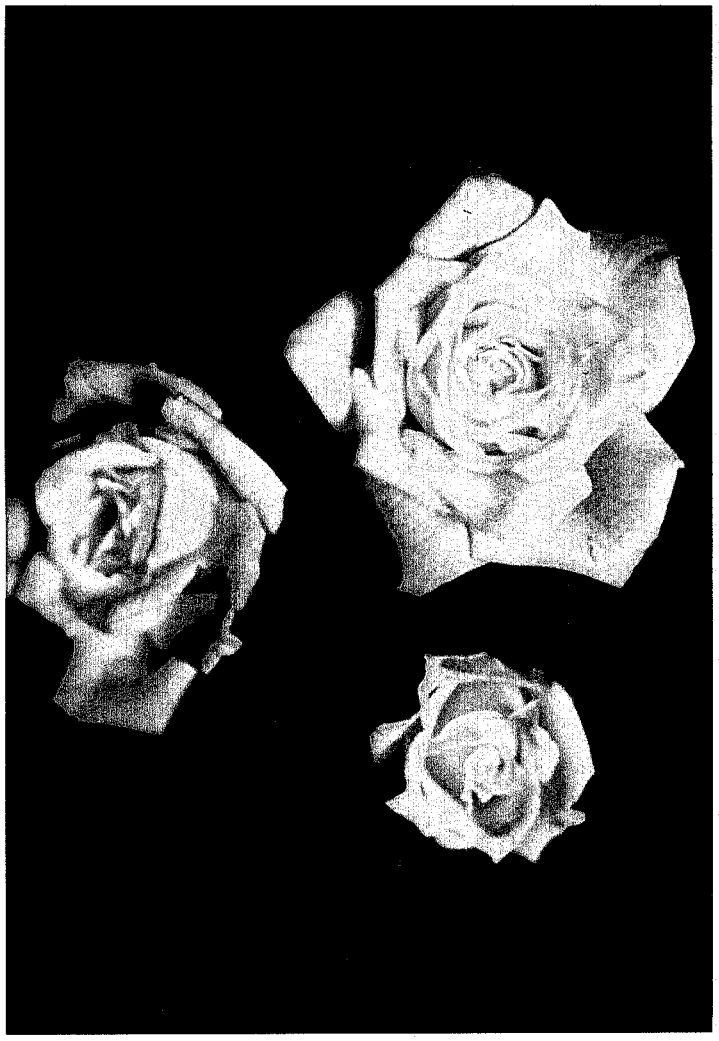

* * * * *